United States Patent
Rauvala et al.

(10) Patent No.: US 9,896,488 B2
(45) Date of Patent: Feb. 20, 2018

(54) PROTAMINE IN TREATMENT OF NEURONAL INJURIES

(71) Applicant: UNIVERSITY OF HELSINKI, University of Helsinki (FI)

(72) Inventors: Heikki Rauvala, Helsinki (FI); Mikhail Paveliev, Helsinki (FI); Juha Kuja-Panula, Otalampi (FI); Ari Rouhiainen, Helsinki (FI); Natalia Kulesskaya, Helsinki (FI)

(73) Assignee: UNIVERSITY OF HELSINKI, Helsinki (FI)

( * ) Notice: Subject to any disclaimer, the term of this patent is extended or adjusted under 35 U.S.C. 154(b) by 0 days.

(21) Appl. No.: 14/899,924

(22) PCT Filed: Jun. 18, 2014

(86) PCT No.: PCT/FI2014/050491
§ 371 (c)(1),
(2) Date: Dec. 18, 2015

(87) PCT Pub. No.: WO2014/202834
PCT Pub. Date: Dec. 24, 2014

(65) Prior Publication Data
US 2016/0272689 A1    Sep. 22, 2016

(30) Foreign Application Priority Data

Jun. 18, 2013 (FI) .................. 20135667

(51) Int. Cl.
C07K 14/46    (2006.01)
A61K 38/17   (2006.01)
C12N 5/0793  (2010.01)

(52) U.S. Cl.
CPC .............. *C07K 14/46* (2013.01); *A61K 38/17* (2013.01); *C12N 5/0619* (2013.01)

(58) Field of Classification Search
None
See application file for complete search history.

(56) References Cited

U.S. PATENT DOCUMENTS

2006/0030548 A1    2/2006    Dong et al.

FOREIGN PATENT DOCUMENTS

| JP | 5-51325 A | 3/1993 |
|---|---|---|
| JP | 2008-133253 A | 6/2008 |
| WO | WO 03/106485 A1 | 12/2003 |
| WO | WO 2004/054594 A1 | 7/2004 |
| WO | WO 2004/103299 A2 | 12/2004 |
| WO | WO 2005/087920 A2 | 9/2005 |
| WO | WO 2007/058902 A1 | 5/2007 |
| WO | WO 2009/020577 A2 | 2/2009 |
| WO | WO 2011/022462 A2 | 2/2011 |
| WO | WO 2011/119608 A1 | 9/2011 |
| WO | WO 2012/112953 A2 | 8/2012 |
| WO | WO 2013/053954 A1 | 4/2013 |

OTHER PUBLICATIONS

Aricescu et al., "Heparan Sulfate Proteoglycans are Ligands for Receptor Protein Tyrosine Phosphatase σ," Molecular and Cellular Biology (Mar. 2002), vol. 22, No. 6, pp. 1881-1892.
Coen, D. M., "The Polymerase Chain Reaction," Current Protocols in Molecular Biology (2001), Supplement 56, pp. 15.0.1-15.0.3.
Coles et al., "Proteoglycan-Specific Molecular Switch for RPTPσ Clustering and Neuronal Extension," Science (Apr. 22, 2011), vol. 332, pp. 484-488.
Collins, F., "Induction of neurite outgrowth by a conditioned-medium factor bound to the culture substratum," Proc. Natl. Acad. Sci. USA (Oct. 1978), vol. 75, No. 10, pp. 5210-5213.
Fry et al., "Corticospinal Tract Regeneration After Spinal Cord Injury in Receptor Protein Tyrosine Phosphatase Sigma Deficient Mice," GLIA (2010), vol. 58, pp. 423-433.
Harris et al., "Chondroitinase ABC Enhances Pericontusion Axonal Sprouting But Does Not Confer Robust Improvements in Behavioral Recovery," Journal of Neurotrauma (Nov. 2010), vol. 27, pp. 1971-1982.
International Search Report dated Sep. 24, 2014, in PCT International Application No. PCT/FI2014/050491.
Jones et al., "The chondroitin sulfate proteoglycans neurocan, brevican, phosphacan, and veriscan are differentially regulated following spinal cord injury," Experimental Neurology (2003), vol. 182, pp. 399-411.
Kwok et al., "Extracellular Matrix and Perineuronal Nets in CNS Repair," Develop. Neurobiol. (2011), vol. 71, pp. 1073-1089.
Miley et al., "High Affinity Binding and Overlapping Localization of Neurocan and Phosphacan/Protein-tyrosine Phosphatase ζ/β with Tenascin-R . . . ," The Journal of Biological Chemistry (Mar. 20, 1998), vol. 273, No. 12, pp. 6998-7005.
Pearson, W. R. and D. J. Lipman, "Improved tools for biological sequence comparison," Proc. Natl. Acad. Sci. USA (Apr. 1998), vol. 85, pp. 2444-2448.
Production of Recombinan Proteins. Novel Microbial and Eukaryotic Expression Systems, Gellissen, G. (ed.) Wiley-VCH Verlag GmbH & Co. KGaA (2005).
Raulo et al., "The Two Thrombospondin Type I Repeat Domains of the Heparin-binding Growth-associated Molecule Bind to Heparin/Heparan Sulfate and Regulate Neurite Extension . . . ," The Journal of Biological Chemistry (Dec. 16, 2005), vol. 280, No. 50, pp. 41576-41583.

(Continued)

*Primary Examiner* — John D Ulm
(74) *Attorney, Agent, or Firm* — Birch, Stewart, Kolasch & Birch, LLP

(57) ABSTRACT

The present invention relates to treatment of neuronal injury. The present invention discloses a novel use of an agent and a novel method for promoting neurite out growth and/or neural regeneration in CNS injuries. A novel mechanism of promoting neurite outgrowth by increasing the interaction of chondroitin sulphate proteoglycan (CSPG) to receptor protein tyrosine phosphatase sigma (RPTPσ) is disclosed.

14 Claims, 5 Drawing Sheets

(56) References Cited

OTHER PUBLICATIONS

Rauvala et al., "Heparin-binding proteins HB-GAM (pleiotrophin) and amphoterin in the regulation of cell motility," Matrix Biology (2000), vol. 19, pp. 377-387.
Rauvala, H. "An 18-kd heparin-binding protein of developing brain that is distinct from fibroblast growth factors," The EMBO Journal (1989), vol. 8, No. 10, pp. 2933-2941.
Search Report dated Mar. 5, 2014, issued in Finnish Patent Application No. 20135667.
Shen et al., "PTPσ is a Receptor for Chondroitin Sulfate Proteoglycan, an Inhibitor of Neural Regeneration," Science (Oct. 23, 2009), vol. 326, pp. 592-596.
Silver, J. and J. H. Miller, "Regeneration Beyond the Glial Scar," Nature (Feb. 2004), vol. 5, pp. 146-156.
Snow et al., "Molecular and Cellular Characterization of the Gilal Roof Plate of the Spinal Cord and Optic Tectum: A Possible Role for a Proteoglycan in the Development of an Axon Barrier, "Developmental Biology (1990), vol. 138, 359-376.
Starkey et al., "Chrondroitinase ABC promotes compensatory sprouting of the intact corticospinal tract and recovery of forelimb function . . . ," European Journal of Neuroscience (2012), vol. 36, pp. 3665-3678.
Written Opinion of the International Searching Authority dated Sep. 24, 2014, in PCT International Application No. PCT/FI2014/050491.
Xiong et al., "Neurorestorative Treatments for Traumatic Brain Injury," Discov. Med. (Nov. 2010), vol. 10, No. 54, pp. 434-442.
Extended European Search Report, dated Dec. 19, 2016, for European Application No. 14812998.4.
Matsunaga et al., "Nucleoprotamine diet derived from salmon soft roe protects mouse hippocampal neurons from delayed cell death after transient forebrain ischemia," Neuroscience Research, vol. 47, No. 3, Nov. 1, 2003, pp. 269-276, XP002981584.

Aggrecan 2µg/ml

Aggrecan 2µg/ml
Protamine peptide 3
0.02mg/ml

A

B

PROTAMINE IN TREATMENT OF NEURONAL INJURIES

REFERENCE TO SEQUENCE LISTING SUBMITTED VIA EFS-WEB

This application includes an electronically submitted sequence listing in .txt format. The .txt file contains a sequence listing entitled "2016-04-08 0837-0403PUS1_ST25.txt" created on Apr. 8, 2016 and is 2,238 bytes in size. The sequence listing contained in this .txt file is part of the specification and is hereby incorporated by reference herein in its entirety.

FIELD OF THE INVENTION

The present invention relates to treatment of neuronal injuries. Specifically, the present invention relates to novel means and mechanisms for promoting neurite outgrowth and/or neural regeneration in diseases in which chondroitin sulfate proteoglycans (CSPGs) have adverse effects on neural regeneration or maintenance, such as injuries of the nervous system.

BACKGROUND OF THE INVENTION

Nervous system injuries affect millions of people every year. As a result of this high incidence of neurological injuries, neuronal regeneration and repair is becoming a rapidly growing field dedicated to the discovery of new ways to recover nerve functionality after injury. The nervous system is divided into two parts: the central nervous system (CNS), which consists of the brain and spinal cord, and the peripheral nervous system (PNS), which consists of cranial and spinal nerves along with their associated ganglia. A brain injury or brain damage is the destruction or degeneration of brain cells in the brain of a living organism. Brain injuries can be classified along several dimensions. Primary and secondary brain injuries are ways to classify the injury processes that occur in brain injury.

Post traumatic regeneration of the brain and spinal cord is a major unsolved medical problem because the brain and spinal cord are not able to regenerate like the peripheral nervous system. While peripheral axons regenerate in patients after nerve injury, brain and spinal cord axons fail to regenerate due to glial scar formation and the inhibitory action of chondroitin sulphate proteoglycans (CSPGs) in the scar. In addition, those factors that promote peripheral nerve regeneration, for instance nerve growth factor, NGF, fail to improve regeneration in the brain and spinal cord. The central nervous system and peripheral nervous system are very different in their reactions to drug treatment and regeneration ability.

Identifying molecular mechanisms guiding neuronal development has been a great challenge. Inhibition of chondroitin sulphate proteoglycans (CSPGs) as a mechanism to enhance neuronal growth has been of considerable interest. CSPGs have been implicated in inhibiting regeneration of axons and dendrites following CNS trauma (Silver and Miller, 2004). CSPGs are also known to be part of the glial scar that forms post-injury, acting as a barrier to prevent axon extension and regrowth. Levels of versican, neurocan, brevican and phosphacan (those CSPGs measured) have all been found to be upregulated after spinal cord injury (Jones et al., 2003).

WO2004/103299 discloses a method of improving functional recovery following a central nervous system contusion injury. The disclosed invention is directed to a method of utilizing chondroitinase (chondroitin sulfate degrading enzyme) to promote autonomic neurological functional recovery following injury in or to the spinal cord. Compositions useful in the method include acceptable formulations of chondroitinase. The method includes administering a therapeutically effective amount of glycosaminoglycan degrading enzyme. The glycosaminoglycan degrading enzyme may be dermatan sulfate or chondroitin sulfate degrading enzymes. The functional recovery may include autonomic functions, sensory functions, motor functions or the like.

WO2005/087920 relates to recombinant and modified chondroitinase ABC I, their production and their uses. The disclosed chondroitinase ABC I enzymes are useful for a variety of purposes, including therapeutic methods such as promoting nerve regeneration, promoting stroke recovery, treating spinal cord injury, treating epithelial disease, treating infections and treating cancer.

Other approaches to CSPG inhibition have focused on the use of molecules/agents that inhibit the interaction of CSPGs with its receptor RPTPσ. WO2011/022462 discloses the use of soluble fragments of RPTPs that bind CSPGs, thus acting as competitive inhibitors to prevent the CSPGs from binding RPTPs on the neuron. The neural cell can be associated with an injury or neurodegenerative condition. WO2012/112953 discloses methods for contacting a neuron with an agent that binds RPTPσ, to thereby induce neuronal outgrowth of the neuron. The agent may induce clustering of RPTPσ and/or inhibit binding of CSPGs to RPTPσ. Examples of suitable agents are heparan sulfate proteoglycan, heparan sulfate, heparan sulfate oligosaccharides, or heparin oligosaccharides.

For nervous system injuries there are substantial patient populations with significant unmet needs, for which novel treatment options are desperately required. There is currently no treatment for recovering human nerve function after injury to the central nervous system. Secondary injury mechanisms have, so far, been predominantly targeted through the use of neuroprotective treatments. However, the compounds and approaches, which have been tested in clinical trials thus far, have disappointingly failed to demonstrate clear efficacy. Consequently, the use of neuroprotective strategies, as the primary treatment option for central nervous system injuries remains in doubt and hence novel approaches are required. Finding out mechanisms and means to promote nerve regeneration is important also clinically, as it is part of the pathogenesis of many diseases. In the hunt for neurostimulatory agents that promote nerve regeneration, well-defined models and analysis methods are required.

BRIEF DESCRIPTION OF THE INVENTION

An object of the invention is thus to provide novel means and mechanisms for promoting neurite outgrowth and/or neural regeneration e.g. in nervous system injuries.

A further object of the invention is to provide a method of promoting neurite outgrowth and/or neural regeneration.

The objects of the invention are achieved by the novel use of protamine or a peptide or a fragment thereof. Furthermore the objects are achieved by providing a novel method of promoting neuronal outgrowth by contacting neuron with protamine, or a peptide or a fragment thereof. The preferred embodiments of the invention are disclosed in the dependent claims.

The invention is based on the surprising realization and unexpected finding that protamine changes the CSPG matrix from regeneration inhibiting to regeneration activating structure. Although protamine sulphate can bind heparin, and is used during cardiopulmonary bypass surgery to neutralise anti-clotting effects, no other clinical uses of protamine have been identified either for use in the treatment of neurodegenerative disease or otherwise.

Moreover, the present application surprisingly discloses that protamine promotes neurite outgrowth and/or neural regeneration by increasing the amount of chondroitin sulphate proteoglycan, CSPG, binding to its receptor RPTPσ. It may have been expected that protamine would sequester the CSPGs from RPTPσ, through interaction of its basic residues with the negatively charged sulphate side chains, but the present inventors found the reverse to be true. Through this novel mechanism, it may be stated that protamine can promote neurite outgrowth by modulating CSPG matrix that leads to its enhanced chondroitin sulphate epitope binding to PTPsigma. Hence, protamine and the novel mechanism of action are advantageous and useful for the treatment of neuronal injuries.

Furthermore, it has surprisingly been found that the novel peptides of the present invention, which are derivable from protamine promote neurite outgrowth effects which are comparable to the wild-type protamine.

An advantage of the invention is that protamine promotes CNS regeneration by converting CSPG-enriched glial scar into permissive milieu for axon and dendrite growth in adult CNS. Additionally, protamine sulphate has already been clinically approved by the FDA and hence safety/toxicity concerns have been addressed.

BRIEF DESCRIPTION OF THE DRAWINGS

In the following the invention will be described in greater detail by means of preferred embodiments with reference to the attached drawings, in which FIG. 1. Alignment of protamine sequences from human (UniProtKB P04553) SEQ ID NO: 11, salmon (UniProtKB P69014) SEQ ID NO: 12, mouse (UniProtKB P02319) SEQ ID NO: 13, rat (UniProtKB P10118) SEQ ID NO: 14, horse (UniProtKB P15341) SEQ ID NO: 15, Killer whale (UniProtKB P24713) SEQ ID NO: 16 and sheep (UniProtKB P68038) SEQ ID NO: 17 show significant similarity. Amino acids are highlighted with greater than 70% identity (black) and similarity (grey).

Figure 3A:
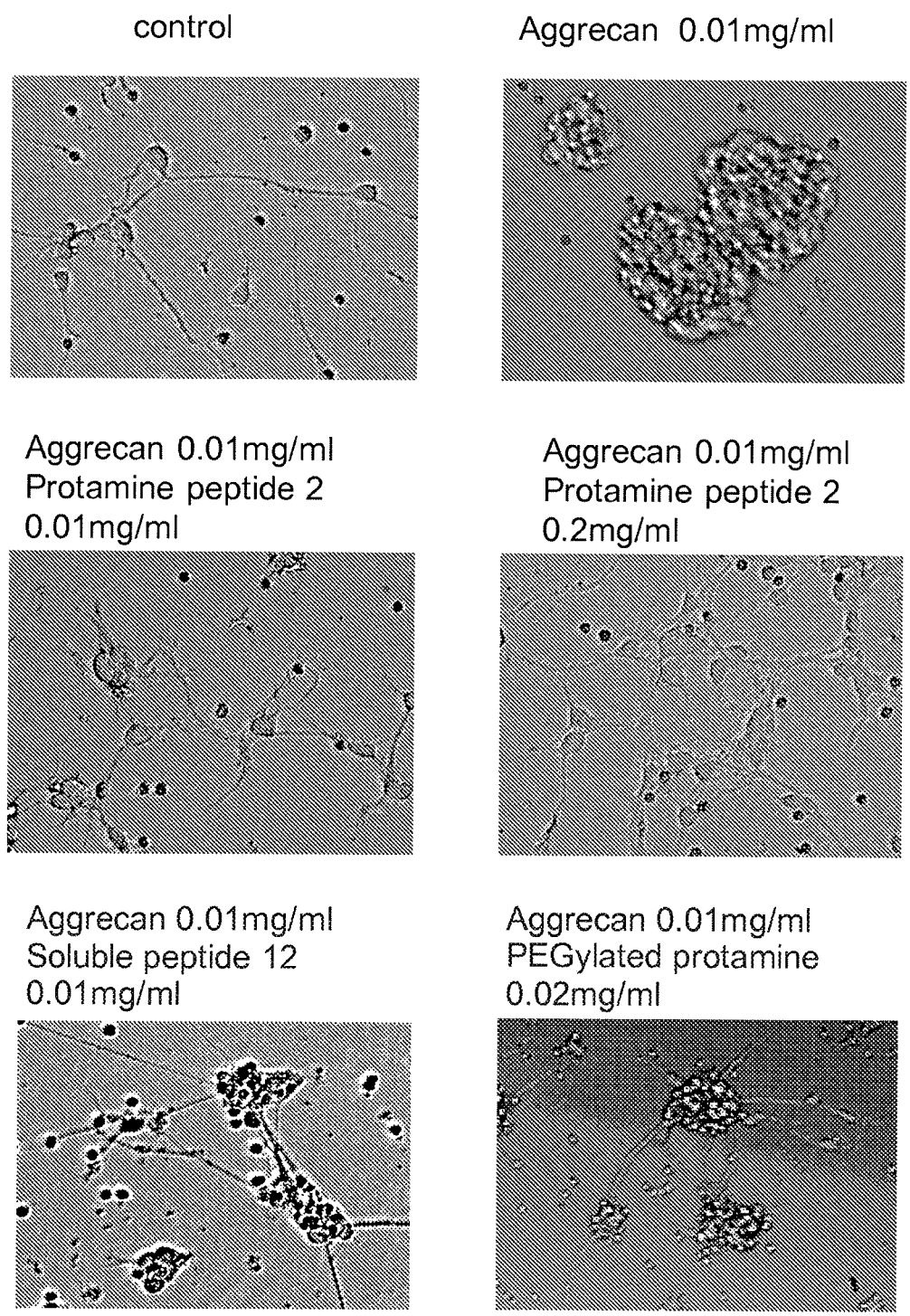
FIG. 3. Peptides derived from protamine promote neurite growth on CSPG-coated substrate in rat cortical neurons in vitro. Chondroitin sulphate proteoglycan aggrecan prevents attachment and neurite growth in embryonic rat cortical neurons (FIG. 3A). Peptide 2 (SEQ ID NO:3,) Peptide 12 (SEQ ID NO: 10) and also pegylated protamine overcome the inhibitory action of aggrecan, promoting neuronal attachment and neurite growth on the aggrecan-coated substrate in vitro.
Figure 3B:
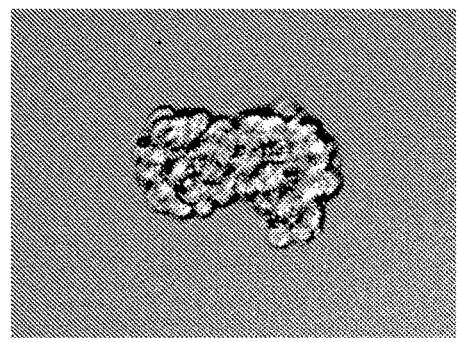

Chondroitin sulphate proteoglycan aggrecan prevents attachment and neurite growth in embryonic rat hippocampal neurons (FIG. 3B). Peptide 3 (SEQ ID NO:4) overcomes the inhibitory action of aggrecan, promoting neuronal attachment and neurite growth on the aggrecan-coated substrate in vitro.

Figure 4:
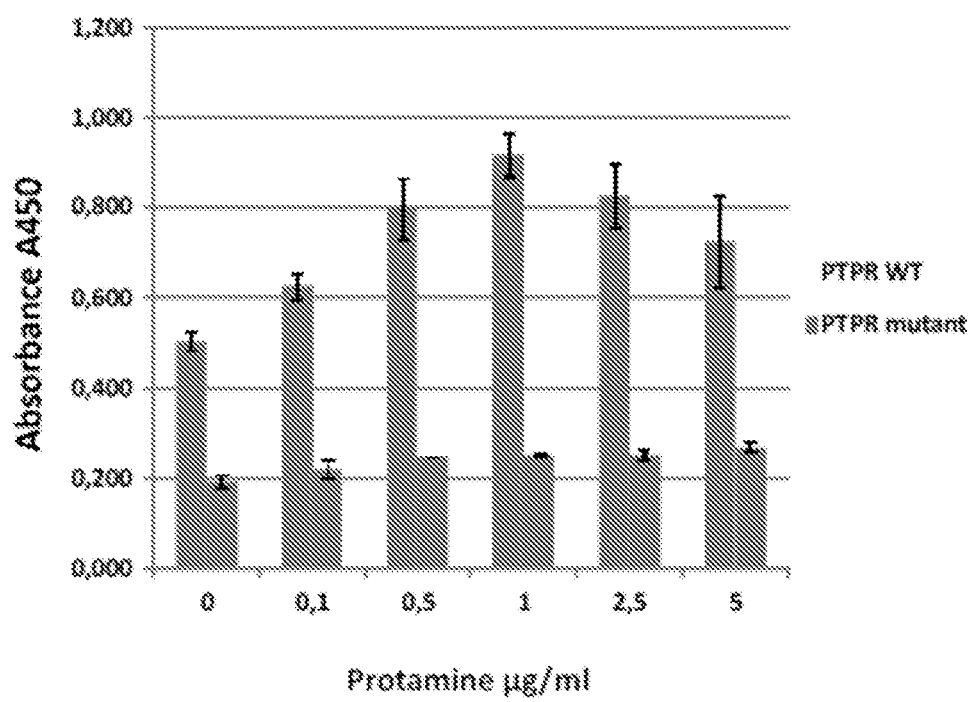

FIG. 4. Protamine increases the amount of aggrecan binding to RPTPσ. Mutant RPTPσ with a defective CSPG-binding site was used as a negative control.

Figure 5:
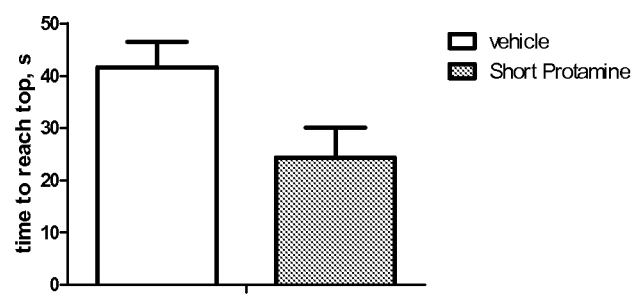
Figure 5:
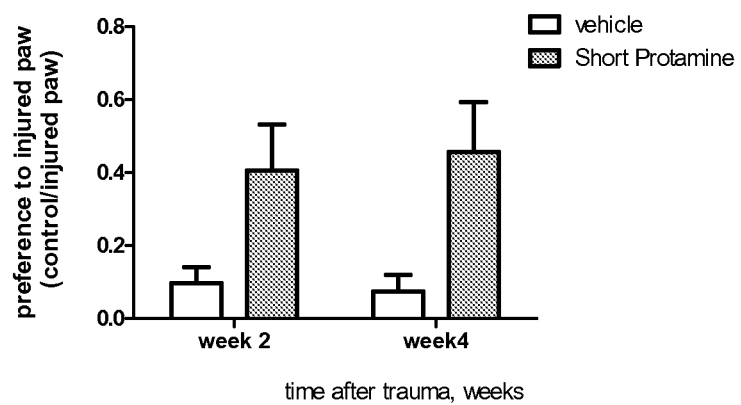

FIG. 5. Peptide 12 (denoted in the figure as short protamine) improves functional recovery as assessed by vertical screen (A) and cylinder (B) behavior tests.

DETAILED DESCRIPTION OF THE INVENTION

Figures 1, 2:
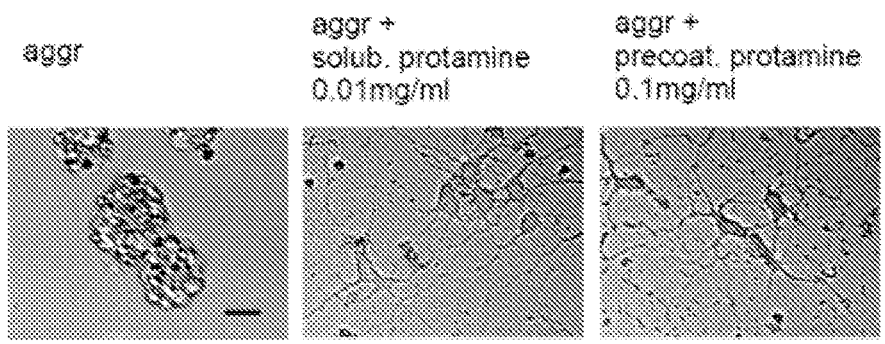
FIG. 2. Protamine promotes neurite growth on CSPG-coated substrate in rat cortical neurons in vitro. Chondroitin sulphate proteoglycan aggrecan prevents attachment and neurite growth in embryonic rat cortical neurons. Protamine overcomes the inhibitory action of aggrecan, promoting neuronal attachment and neurite growth on the aggrecan-coated substrate in vitro.

The present invention relates to a use of protamine or a fragment thereof for treating injuries of the nervous system in a subject. Specifically, the present invention relates to a use of protamine or a fragment thereof as anti-CSPG therapy in diseases in which the CSPGs restrict neuronal regeneration or maintenance. According to the invention protamine promotes neurite outgrowth and neuronal attachment on CSPG-coated substrate by overcoming the inhibitory action of CSPG (FIG. 2). Furthermore according to one embodiment of the invention protamine increases the interaction of chondroitin sulphate proteoglycan (CSPG) to the receptor protein tyrosine phosphatase sigma (RPTPσ) (FIG. 4), thereby promoting the neurite outgrowth.

The present invention relates also to a protamine peptide consisting of an amino acid sequence set forth in SEQ ID NO: 3, or its variant. Furthermore, the present invention relates to the use of a protamine peptide consisting of an amino acid sequence according to SEQ ID NO: 3 as a medicine.

The present invention relates also to the use of a protamine peptide consisting of an amino acid sequence set forth in SEQ ID NO: 3 or its variant in treating neuronal injuries in a subject.

According to the present invention protamine or a peptide or fragment thereof is used in treating neuronal disorders, which include disease, disorder, or condition directly or indirectly affecting the normal functioning or anatomy of a subject's nervous system. The disorder may be a neuronal injury, which can be acute or chronic. Examples of acute injury are those that result from surgery, trauma, compression, contusion, transection or other physical injury, vascular pharmacologic or other insults including hemorrhagic or ischemic damage. Chronic neuronal injury may result from repetitive stress, inflammation/oxidative stress within a neural tissue caused by disease, neurodegenerative or other neurological diseases.

According to the present invention protamine or a peptide or fragment thereof is beneficial in all diseases where the CSPG matrix is inhibitory for regeneration or maintenance of axons and dendrites. In one embodiment of the present invention the disease is a neuronal injury selected from a group consisting of neurodegenerative diseases, traumatic brain injury, spinal cord injury, multiple sclerosis (MS), amyotropic lateral sclerosis (ALS), Parkinson's disease, stroke, peripheral nerve injury, eye injury and skin burn. Preferably the neuronal injury is TBI or SCI.

Protamines are small, arginine-rich, nuclear proteins that replace histones late in the haploid phase of spermatogenesis and are believed to be essential for sperm condensation and DNA stabilisation. Protamine has been shown to be able to condense plasmid DNA efficiently for delivery into several different types of cells. Protamine sulfate is a commonly used salt form of protamine.

Gene and protein sequences have been determined for protamines of numerous vertebrate species. Mice, humans and certain fish have two or more different protamines, whereas the sperm of rabbits, for example, have only one form. The two human protamines are denoted by PRM1 (UniProtKB P04553) and PRM2 (UniProtKB P04554), whilst examples of protamines from fish include salmine from salmon (UniProtKB P69014), clupeine from herring (UniProtKB P69010) and iridine from rainbow trout (UniProtKB P02328). FIG. 1 shows a sequence alignment of protamines derived from different species and demonstrates the significant amount of conservation throughout the amino acid sequences.

Protamine sulphate can bind heparin and is mandatorily used during cardiopulmonary bypass surgery to neutralise the anti-clotting effects of heparin. It is estimated that over two million patients are exposed to the heparin-protamine interaction per year, where 1 mg of protamine sulphate (i.v.) is administered for every 100 IU of active heparin. Protamine neutralization of heparin can cause increased pulmonary artery pressures and decreased systolic and diastolic blood pressure, myocardial oxygen consumption, cardiac output, heart rate, and systemic vascular resistance. These multiple cardiovascular effects are mediated via complement activation, histamine release, thromboxane and nitric oxide production, and antibody formation (Carr and Silverman). Since protamine is a highly cationic peptide, it can bind to heparin to form a stable ion pair, which does not have anticoagulant activity. The complex of heparin-protamine is then removed and broken down by the reticuloendothelial system.

Protamine has also been used in gene transfer, protein purification and in tissue cultures as a crosslinker for viral transduction.

According to the present invention protamine may have eg. a sequence set forth by SEQ ID NO: 1 or any other similar sequence. The present invention relates also to the use of fragments of protamine. As used herein "a fragment" refers to any part of protamine that is long enough to have the desired activity of neurite outgrowth. In a preferred embodiment of the invention, protamine or a fragment thereof is native, i.e. a protein in its natural state, unaltered by heat, chemicals, enzyme action, or the exigencies of extraction.

According to the present invention "a variant" of protamine peptide may comprise amino acid substitutions, deletions or insertions, but it still functions in a substantially similar manner to the protamine peptide defined above. The peptides of the present invention and variants thereof may be fused to other proteins, polypeptides or peptides (N- or C-terminally), or conjugated to other substances. The peptides of the present invention may also be bound or conjugated to substances which enhance their ability to pass through the blood brain barrier. According to one embodiment of the present invention also peptides are encompassed which exhibit at least 80%, 85%, 90%, 95%, 96%, 97%, 98% or 99% identity with the peptide having SEQ ID NO:3. Whether any two amino acid molecules have amino sequences that are at least, for example, 80%, 85%, 90%, 95%, 96%, 97%, 98% or 99% "identical", can be determined using known computer algorithms such as the "FASTA" program, using for example, the default parameters as in Pearson et al. (1988) PNAS USA 85: 2444.

As used herein, the term "neurite growth" or "neurite outgrowth" includes the process by which axons or dendrites extend from a neuron. The outgrowth can result in a new neuritic projection or in the extension of a previously existing cellular process. Neurite outgrowth may include linear extension of an axonal process by five cell-diameters or more. "Central nervous system (CNS) neurons" include the neurons of the brain, the cranial nerves and the spinal cord. The invention relates not only to CNS neurons but also to peripheral neurons that make projections (axons) in CNS, for instance dorsal root ganglion neurons.

As used herein the term "brain injury" is the destruction or degeneration of brain cells is in the brain of a living organism. Brain injuries can result from direct impacts to the head. Such injuries are for example traumatic brain injury and spinal cord injury. The present invention may also be used in treating other neuronal disorders, which include disease, disorder, or condition directly or indirectly affecting the normal functioning or anatomy of a subject's nervous system. The disorder may be a neuronal injury, which can be acute or chronic. Examples of acute injury are those that results from surgery, trauma, compression, contusion, transection or other physical injury, vascular pharmacologic or other insults including hemorrhagic or ischemic damage. Chronic neuronal injury may result from repetitive stress, inflammation/oxidative stress within a neural tissue caused by disease, neurodegenerative or other neurological diseases. The invention can be beneficial in all diseases where the CSPG matrix is inhibitory for regeneration or maintenance of axons, such as TBI, SCI, multiple sclerosis (MS disease) and amyotrophic lateral sclerosis (ALS).

"Traumatic brain injury, TBI" as used herein includes the condition in which a traumatic blow to the head causes damage to the brain or connecting spinal cord, with or without penetrating the skull. It relates more specifically to the actual mechanical damage that occurs at the type of trauma, such as shearing, tearing and stretching of axons, neurons and blood vessels. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

"A spinal cord injury, SCI" as used herein is damage to any part of the spinal cord or nerves at the end of the spinal canal. It often causes permanent changes in strength, sensation and other body functions below the site of the injury. The spinal cord injury may be a complete severing of the spinal cord, a partial severing of the spinal cord, or a crushing or compression injury of the spinal cord. Spinal cord injury SCI proceeds over minutes, hours, days and even months after the initial traumatic insult and can lead to significant expansion of the original damage. These secondary events are a consequence of delayed biochemical, metabolic and cellular changes, which are initiated by the primary injury, and includes inflammation, free radical induced cell death and glutamate excitotoxicity.

Axonal sprouting, from surviving neurons, is associated with spontaneous motor and sensory recovery following TBI and SCI. Although the CNS has a limited capacity to regenerate, spontaneous pericontusional axon sprouting does take place approximately 1-2 weeks after trauma. However, this process typically fails due to an inhibitory axonal environment promoted by chondroitin sulphate proteoglycans (CSPGs). Astrocytes, at the site of injury, produce CSPGs, beyond which the axons cannot regenerate (Silver and Miller, 2004). Inhibition of CSPG activity represents one potential approach to neuroregeneration, following either TBI or SCI. Evidence in support of this theory has been provided through the use of chondroitinase ABC (ChABC, an enzyme that degrades CSPGs) at the site of trauma in rodent models of TBI and SCI. ChABC treatment resulted in an enhanced and prolonged sprouting response with an increase in sensory, motor and autonomic function (Harris et al., 2010, Starkey et al., 2012).

Multiple sclerosis (MS) is a chronic immune-mediated disease that is characterized by demyelinating and degenerative processes within the central nervous system. MS potentially requires symptomatic and disease-modifying therapies. Numerous symptoms such as fatigue, spasticity, depression, bowel and bladder dysfunction, pain, and impaired mobility are associated with the neurologic damage that results from MS. Several therapies e.g. modafinil, dalfampridine, baclofen, diazepam, gabapentin, opioids are used for symptomatic treatment of disability and symptoms, but these do not improve disease outcome. Intravenous corticosteroids are used in the management of MS exacerbations, but do not appear to affect the degree of improvement from acute exacerbations. A more definitive therapy for MS should reduce relapse rate, prolong remission, limit the onset of new MS lesions, and postpone the development of long-term disability. There are currently available MS disease-modifying therapies, but thus far no beneficial agent has been established in primary-progressive MS.

Amyotrophic lateral sclerosis (ALS), also referred to as motor neuron disease and Lou Gehrig's disease, is the most common form of the motor neuron diseases. The disorder is characterized by rapidly progressive weakness, muscle atrophy, twitching and spasticity, difficulty with speaking and swallowing and a decline in breathing ability. The defining feature of ALS is the death of both upper and lower motor neurons in the motor cortex of the brain, the brain stem, and the spinal cord. The disease has its onset usually in midlife and leads to death within 3-5 years from diagnosis, usually due to respiratory failure. Once diagnosed, only 10% of patients survive for longer than 10 years. In the US, there are approximately 30,000 ALS sufferers, with 5,000 new cases each year. Although there are currently several ongoing clinical trials for novel ALS treatments, there is no curative therapy for ALS and palliative care remains the most important means of treatment.

"Chondroitin sulphate proteoglycans, CSPGs" as used herein, represent a varied class of complex extracellular matrix macromolecules. They share a general molecular structure comprising a central core protein with heavily sulphated sugar side chains, usually glycosaminoglycans (GAGs), attached through covalent bonds. The GAG side chains are of different lengths, which partially define the different CSPGs e.g. aggrecan (CSPG1), versican (CSPG2), neurocan (CSPG3), brevican (CSPG7) and phosphacan. Some of these aggrecans share similar N-terminal and C-terminal domains.

CSPGs play an active role in the neural development of postnatal babies, acting as guidance cues for developing growth cones. Growing axons are found to avoid CSPG dense areas. Similarly, CSPGs found near and around embryonic roof plates inhibit axon elongation through the spinal cord and direct the axons in an alternative direction. CSPGs absent on roof plates were found to attract axonal elongation (Snow et al., 1990).

According to the present invention protamine promotes neurite outgrowth on CSPG coated substrate. The CSPG-coated substrate is an experimental model of a CSPG matrix. It can be made for example by coating a CSPG, like aggrecan, on a tissue culture well. Anti-CSPG effects in vivo using chondroitinase ABC were originally found using in vitro assays (Kwok J C et al 2011). As used herein the CSPG matrix means the type of extracellular matrix that expresses chondroitin sulphate proteoglycans. The extracellular matrix (ECM) provides a number of critical functions in the CNS, contributing both to the overall structural organization of the CNS and to control of individual cells. At the cellular level, the ECM affects its functions by a wide range of mechanisms, including providing structural support to cells, regulating the activity of second messenger systems, and controlling the distribution and local concentration of growth and differentiation factors. The brain extracellular matrix has trophic effects on neuronal cells and affect neurite outgrowth.

Only recently has a receptor, protein tyrosine phosphatase sigma (RPTPσ) been identified for the CSPGs (Shen et al., 2009). It was previously demonstrated that disruption of the RPTPσ gene enhanced regeneration in sciatic nerves, but the mechanism by which this was achieved was unclear. An interaction was demonstrated between both neurocan and aggrecan with RPTPσ, which was dependent upon the chondroitin sulphate side chains. RPTPσ has a conserved, positively charged, region in the first immunoglobulin domain that is known to interact with heparin sulphate (Arisescu et al., 2002). Mutation of a cluster of four lysine residues in this area to alanines, reduced binding of CSPG to RPTPσ to background levels.

A functional effect of the RPTPσ and CSPG interaction, has been demonstrated by using dorsal root ganglion (DRG) neurons that constitutively express high levels of RPTPσ. Wild-type DRG neurons were cultured, in parallel with those from mice with a targeted gene disruption of RPTPσ, in the presence of a CSPG mixture. Control DRG neuron outgrowth was reduced by approximately 50% in the presence of the CSPG mixture, but had far less effect on those neurons from RPTPσ$^{-/-}$ mice. When the DRG neurons were challenged with purified neurocan, similar results were observed.

The role of RPTPσ in inhibiting regeneration of axons and dendrites, through CSPG interaction, following injury has also been demonstrated using appropriate in vivo models. In PTPσ$^{-/-}$ mice, following a dorsal column crush injury, axonal extension into the lesion penumbra was significantly improved, compared to controls (Shen et al., 2009). The ability of corticospinal tract (CST) axons to regenerate after spinal hemisection and contusion injury in PTPσ$^{-/-}$ mice has also been assessed. Damaged CST fibers, in PTPσ$^{-/-}$ mice, were found to regenerate and extend for long distances after injury to the thoracic spinal cord. In contrast, no long distance axon regeneration of CST fibers was seen after similar lesions in wild-type mice (Fry et al., 2010).

RPTPσ is also known to bind heparan sulphate proteoglycans (HSPGs), which are similar to the CSPGs, in that they contain a protein core with heavily sulphated, negatively charged, sugar side chains. Although CSPGs, through RPTPσ, have been shown to have an inhibitory effect on neuronal outgrowth, HSPGs, also acting through RPTPσ, have been shown to strongly promote neuronal growth (Coles et al., 2011). Both CSPGs and HSPGs bind to a common site on RPTPσ and these differential effects were rationalised based on RPTPσ oligomerisation status. Heparan sulphate GAGs were found to induce oligomerisation of RPTPσ fragments, but chondroitin sulphate GAGs did not support clustering. HSPGs and CSPGs differ in the composition of their GAG chains; sulphate groups are more evenly distributed in CSPGs, whereas HSPGs contain areas of high sulphation. Receptor oligomerisation may cause microdomains with high phosphotyrosine levels and support neuronal extension, which CSPGs are able to disrupt and hence inhibit axon growth (Coles et al., 2011).

In the present invention the protamine or a peptide or fragment thereof is used for treating of neuronal injuries. Treating and treatment refers to increasing, enhancing and promoting neuron regeneration and/or nerve growth in the presence of a neuronal injury. Treating and treatment encompass both therapeutic and prophylactic treatment regimens.

According to one aspect of the present invention protamine or the peptide or fragment thereof may be formulated in a pharmaceutical preparation, which can be administered to a subject for preventing or treating neuronal injuries. The pharmaceutical preparation may further comprise any other therapeutically effective agents and any other agents such as pharmaceutically acceptable excipients, carriers, buffers, adjuvants, antiseptics, fillings, stabilizing and thickening agents and or any components well known in the art.

In a preferred embodiment of the present invention a subject is a human or and animal.

The present invention also relates to a method of promoting neuronal outgrowth and/or neural regeneration. This is achieved by contacting the neuron with a therapeutically effective amount of protamine or a fragment thereof or the peptide of the invention. The contacting can occur in vitro or in vivo to the neuronal cell. In vitro, protamine can be added to a cell culture containing the neuron. In vivo protamine can be administered to a subject, such that an effective amount of it comes in contact with the neuron to thereby induce the neuronal outgrowth. In one embodiment, the neuron is a central nervous system neuron.

The term "administered" or "administering" to a subject includes dispensing, delivering or applying the agent to the subject by any suitable route for delivery of the agent to a site in the body where neuronal outgrowth is desired. Protamine can be administered directly to the nervous system (particularly to the site of injury), intracranially, intraspinally, intracerebroventricularly, intravenously, topically or intrathecally, e.g. into a chronic lesion of a neurodegenerative disease or at the site(s) of traumatic injury.

The term "administered" or "administering" to a subject includes dispensing, delivering or applying the agent to the subject by any suitable route for delivery of the agent to a site in the body where neuronal outgrowth is desired. Protamine may be delivered according to any known method in the art. These include, without limitation, subcutaneous, intramuscular, transdermal, intravenous, oral, sublingual, nasal, rectal and topical administrations. In one embodiment of the invention PEGylation of protamine is used to modify pharmacokinetics of a drug and its interaction with living tissues. PEGylation of protamine sulfate enhances its ability to promote neurite growth on CSPG-substrate in cortical neurons.

One preferred method of administration is to introduce protamine or a peptide or fragment thereof to the site of injury in a surgical operation. Another preferred method of administration is to introduce protamine to the site of injury without open surgery, e.g. by injection. Preferably protamine is administered via direct injection or protamine-bound carrier (scaffold) material implantation or viral vector expressing protamine under a cleavable secretion signal engineered in the construct. The scaffolds may include natural components (aggrecan, neurocan, hyaluronic acid) or artificial materials. The route of administration and the dosage regimen will be determined by skilled clinicians, based on factors such as the exact nature of the condition being treated, the severity of the condition, and the age and general physical condition of the patient.

In one embodiment, administration is to thereby contact injured and/or non-injured neurons proximal to the injury site. In one embodiment, administration is such as to deliver the agent across the blood brain barrier. The agent of the present invention may be formulated as part of pharmaceutical compositions comprising one or more of the specific agents.

The term "effective amount" or "therapeutically effective amount" refers to the amount of an active agent sufficient to induce a desired biological result e.g. promotion and/or restoration of neuronal regeneration and/or neurite growth. That result may be alleviation of the signs, symptoms, or causes of a disease, or any other desired alteration of a biological system.

Neuronal outgrowth induced by the methods described herein can be determined by a variety of methods, such as by determination of the formation of axons (e.g., detecting the formation of neuronal branching microscopically or by showing cytoplasmic transport of dyes). Neuronal outgrowth can also be detected by determination of the formation of neural connectivity. Outgrowth can also be determined by an increase or a restoration of function of the neuron. Neuronal function can be measured by standard assays such as detection of action potential or nerve impulse condition by standard assays.

EXAMPLES

Reagents and Chemicals

Protamine (salmon) and protamine sulphate (herring) were from Sigma, protamine sulphate (salmon) was from Leo Pharma. Bovine aggrecan was from Sigma. The DNA sequence (the template cDNA clone MGC: 63375 IMAGE: 6834684) of the CSPG-binding domain of mouse RPTPσ was used for Fc-tagged RPTPσ protein production. Peptides derived from the protamine sequence were custom synthesised by CASLO ApS (Denmark).

Neurite Outgrowth Assay

Cortical or hippocampal neurons from E17 rat embryos were plated at 50,000 cells/cm2 on plastic cell culture plates. Plates were precoated with aggrecan or IgG (10 µg/ml). Protamine, or derived peptides, were precoated together with aggrecan or added to culture medium when plating neurons. Cells were cultured for 1.5-3.5 days and after that images of cell cultures were taken using phase contrast microscope with ×20 objective. Neurite length was quantified using ImagePro software. Mouse neurons were immunostained with anti-tubulin βIII antibodies and imaged using fluorescent microscope.

RPTPσ Binding Assay

The Fc-tagged extracellular domain of RPTPσ was immobilized on protein G-coated plates. Binding of biotinylated aggrecan to RPTPσ was quantified via colorimetric assay using streptavidin-conjugated horse radish peroxidise. Experiments were done by using protein G coated 96 well plates (Pierce, prod. #15133). Wells were first washed briefly with PBS, 0.05% Tween-20 solution. RPTPσ wild type and mutant FC-fusion proteins were diluted into 2 µg/ml solution in buffer containing PBS, 1% BSA, 0.05% Tween-20. 150 µl of protein solution was added into the wells and plates were left for shaking at +RT for 1 hour. Wells were washed 3 times 5 minutes with 200 µl of PBS, 0.05% Tween-20. During the coating and washing steps biotinylated Aggregan was diluted to 5 µg/ml with different amounts of protamine (0-5 µg/ml) in solution containing PBS, 1% BSA, 0.05% Tween-20. Aggeregan and protamine were left together with shaking for 30 minutes before applying 150 µl of this solution into the washed RPTPσ coated wells. Wells were left for shaking at +RT for 1 hour. Wells were washed 3 times 5 minutes with 200 µl of PBS, 0.05% Tween-20. Streptavidin-Peroxidase Polymer (SIGMA, S2438) was diluted 1/10 000 into PBS, 1% BSA, 0.05% Tween-20 solution and 150 µl was applied into the washed wells which were left for shaking +RT for 30 minutes. Wells were washed 3 times 5 minutes with 250 µl of PBS, 0.05% Tween-20. Detection of bound Streptavidin-Peroxidase Polymer was done by adding 200 µl of OPD (o-Phenylenediamine dihydrochloride, SIGMA P9187) substrate into the wells and was measured by reading the absorbance at 450 nm (A450).

Example 1—Protamine Promotes Neurite Outgrowth on Aggrecan Substrate In Vitro

Chondroitin sulphate proteoglycan aggrecan prevents attachment and neurite growth in embryonic rat cortical neurons in culture. Protamine overcame this inhibitory action of aggrecan, promoting neuronal attachment and neurite growth on the aggrecan-coated substrate in vitro. Protamine was active as both the free protein and as sulphate salt (FIG. 2).

Figure 3B:
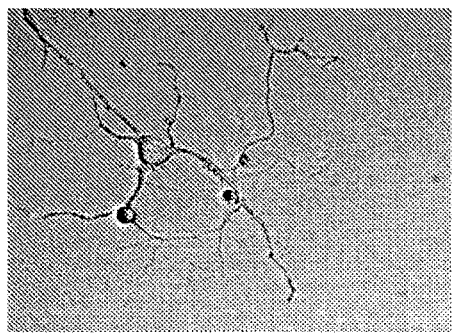

Example 2—A Peptide Derived from the Protamine Sequence Promotes Neurite Outgrowth on Aggrecan Substrate In Vitro Due to the activity displayed by protamine, a series of peptides (Table 1), based on the protamine sequence, were synthesised and tested in the neurite outgrowth assay. Peptides 2 (SEQ ID NO:3) and peptide 12 (SEQ ID NO. 10) displayed activity (FIG. 3).

TABLE 1

Peptides derived from the protamine sequence

| Peptide | Sequence |
| --- | --- |
| Protamine (salmon), SEQ ID NO: 1 | MPRRRRSSSRPVRRRRRPRVSRRRRRRGGRRRR |
| Peptide 1, SEQ ID: 2 | ARRRRS |
| Peptide 2 SEQ ID: 3 | SRPVRRRRRPRVSRRRRRRGGRRRR |
| Peptide 3 SEQ ID: 4 | SRPVRRRRRPRVS |
| Peptide 4 SEQ ID: 5 | SRRRRRRG |
| Peptide 5 SEQ ID: 6 | RRRRRR |
| Peptide 6 SEQ ID: 7 | RRRR |
| Peptide 7 | RR |
| Peptide 10 SEQ ID: 8 | AKKKKS |
| Peptide 11 SEQ ID: 9 | KKKKKK |
| Peptide 12 SEQ ID: 10 | VSRRRRRRGGRRRR |

Example 3—Protamine Increases Aggrecan Binding to RPTPσ

Aggrecan binding to RPTPσ was assessed via ELISA using Fc-tagged RPTPσ and biotinylated aggrecan. Binding was quantified using streptavidin-bound horse radish peroxidase. Mutant RPTPσ, with a defective CSPG-binding site, was used as a negative control. Protamine was found to increase aggrecan binding to wild type RPTPσ, by two fold, in a concentration-dependent manner. By contrast, aggrecan binding to mutant RPTPσ was not affected by protamine (FIG. 4).

Example 4—Pegylated Protamine Sulphate has Higher Activity to Promote Neurite Growth than Protamine Sulphate PEGylation of pharmaceutical compounds is often used to modify pharmacokinetics of a drug and its interaction with living tissues. Here it is demonstrated that protamine keeps active upon PEGylation so that PEGylated protamine induces neurite growth on CSPG-coated substrate (FIG. 3). The pegylation was done according to the following procedure: Protamine was buffered with 1×PBS in concentration of 9 mg/ml; 10 times molar excess of mPEG-NHS (Nanocs Inc.) was added on the Protamine solution; crosslinking of mPEG-NHS to Protamine was carried out 2 hours in room temperature with shaking; excess of mPEG-NHS was quenched by adding 100 mM Tris-HCl pH 7.5 for 1 hour in room temperature with shaking and PEGylated Protamine was purified with Heparin-sepharose chromatography by using salt gradient for elution.

Example 5—Protamine Peptide 12 Promotes Functional Recovery Following SCI

Nerve tracts of one side of the spinal cord were cut (hemisection) at the C4 level, which causes reduced locomotor functions as seen in vertical climbing and usage of the limb on the affected side (represented in the cylinder test). When protamine peptide 12 is given by intracerebroventricular injection, the time used in the vertical climbing test becomes shortened compared to injection of the vehicle only, indicating improved basic locomotion in the group of mice treated with peptide 12 (FIG. 5A). Furthermore, protamine peptide 12 enhances limb usage on the affected side compared to the vehicle (FIG. 5B), which also indicates improved healing due to protamine peptide 12.

Spinal Cord Injury and Post-Operation Care

Animals were anaesthetized with a intraperitoneal mixture of Ketaminol (2 mg/20 g body weight, Intervet) and Rompun (0.25 mg/20 g body weight, Bayer). After laminectomy at C5 vertebral level, the dura was carefully removed. The right cervical spinal hemicord was transected with a 25G syringe needle from midline dorsal vessel to the lateral side. Bleeding was controlled with haemostatic gelatin sponge. Muscle and skin were sutured with 6-0 monocryl. 30 min before surgery and during following 3 days mice were treated with antibiotic Borgal (30 mg/kg, Intervet). Body weight and bladder expression were checked for 7 days, and animal received Rimadil (5 mg/kg, Pfizer) and Rapidexon (0.2 mg/kg, Evrovet) to control pain and inflammatory swelling until they stop to lose body weight.

Behavioral Assessment of Functional Recovery

Vertical Screen (VS).

The mouse was placed on a very brink of horizontal wire screen (25×22 cm, diameter of wires 2 mm spaced at 1 cm) faced to edge. Immediately after that the screen was turned vertically to place mouse to upside down position at the lower edge. The time that animal was needed to climb to the upper edge were measured during 1 min. This test was repeated every second week starting from 1st week after surgery.

Assessment of Forelimb Use.

Based on the test of abnormal posture of suspended animal applied on animal stroke model by Hoffer (J Cereb Blood Flow Metab, 2013) and Bederson (Stroke, 1986) we developed scoring system to assess the severity of forelimb dysfunctions after cervical hemisection. Mouse was held gently by tail suspended under the grid and then slowly pulled down to allow gripping the grid by front paws. The flexion of forelimbs in suspended position and the effectiveness and accuracy of gripping were used for score judgment according the criteria presented in Table 2.

TABLE 2

Criteria for score judgment

| score | criteria |
|---|---|
| 0 | mouse extent both forelimbs straight in suspended position and tightly grip the grid |
| 1 | mouse keep the ipsilateral to trauma site forelimb slightly flexed, but the grid gripping is tight and accurate |
| 2 | mouse keep the ipsilateral to trauma site forelimb flexed, grid gripping is weak and mouse can make multiple paw misplacement before gripping |
| 3 | mouse keep the ipsilateral to trauma site forelimb flexed and does not use it in gripping |

Cylinder Test of Limb Use Asymmetry.

Mouse was placed to glass cylinder 10 cm in diameter and 14 cm high. Mirror was position at the angle behind of cylinder for better observation. Mouse was videotaped for the first 20 exploratory vertical rearing or for 5 min. The number of rearing in which mouse used right (impaired), left or both limbs for support against the wall were measured. Paw preference were calculated as ratio of total number of left limb use (left+both) to total number of right (impaired) limb use (right+both).

Statistic.

Data obtained from Vertical screen test were analyzed by one-way ANOVA followed by post-hoc Newman-Keuls test for detection of group differences. Nonparametric Mann-Whitney test was used for analyses of score assessment of forelimb use and cylinder test.

It will be obvious to a person skilled in the art that, as the technology advances, the inventive concept can be implemented in various ways. The invention and its embodiments are not limited to the examples described above but may vary within the scope of the claims.

REFERENCES

Xiong Y. et al., Neurorestorative treatments for traumatic brain injury. Discovery Medicine (2010) 10 434-442.

Silver and Miller, Regeneration beyond the glial scar. Nature Reviews Neuroscience (2004) 5 146-156.

Harris N. et al., Chondroitinase ABC enhance pericontusion axonal sprouting but does not confer robust improvements in behavioural recovery. Journal Neurotrauma (2010) 27 1971-1982.

Starkey M. L. et al., Chondroitinase ABC promotes compensatory sprouting of the intact corticospinal tract and recovery of forelimb function following unilateral pyramidotomy in adult mice. European Journal Neuroscience (2012) 36 3665-3678.

Snow D. M. et al., Molecular and cellular characterization of the glial roof plate of the spinal cord and optic tectum: a possible role for a proteoglycan in the development of an axon barrier. Developmental Biology (1990) 138 359-376.

Jones, L. L. et al., The chondroitin sulfate proteoglycans neurocan, brevican, phosphacan, and versican are differentially regulated following spinal cord injury. Experimental neurology (2003) 182 399-411.

Shen Y. et al., PTPσ is a receptor for chondrotin sulphate proteoglycan, an inhibitor of neural regeneration. Science (2009) 326 592-596.

Aricescu A R et al., Heparan sulphate proteoglycans are ligands for receptor protein tyrosine phosphatase sigma. Molecular Cellular Biology (2002) 22 1881-1892.

Fry E. J. et al., Corticospinal tract regeneration after spinal cord injury in receptor protein tyrosine phosphatase sigma deficient mice. Glia (2010) 58 423-433.

Coles C. H., Proteoglycan-specific molecular switch for RPTPσ clustering and neuronal extension. Science (2011) 332 484-488.

Rauvala, H., An 18-kd heparin-binding protein of developing brain that is distinct from fibroblast growth factors. EMBO Journal (1989) 8 2933-2941.

Rauvala H. et al., Heparin-binding proteins HB-GAM (pleiotrophin) and amphoterin in the regulation of cell motility. Matrix Biology (2000) 19 377-387.

Raulo et al., The two thrombospondin type 1 repeat domains of the heparin-binding growth-associated molecule bind to heparin/heparin sulphate and regulate neurite extension and plasticity in hippocampal neurons. Journal of Biological Chemistry (2005) 280 41576-41583.

Milev P. et al., High affinity binding and overlapping localisation of neurocan and phosphacan/protein tyrosine phosphatase-ζ/β with Tenascin-R, amphoterin and HB-GAM. Journal of Biological Chemistry (1998) 273 6998-7005.

Sambrook J and D W Russell. 2001. Molecular cloning, a laboratory manual. Cold Spring Harbor Laboratory, New York, US.

Coen, D. M. (2001) The polymerase chain reaction. In: Ausubel, F. M., Brent, R., Kingston, R. E., More, D. D., Seidman, J. G., Smith, K. and Struhl, K. (eds.) Current protocols in molecular biology. John Wiley & Sons. Inc., Hoboken, USA.

Gellissen, G. (ed.) (2005) Production of recombinant proteins. Novel microbial and eukaryotic expression systems. Wiley-VCH Verlag Gmbh & Co. Weinheim, Germany.

Kwok J C, Dick G, Wang D, Fawcett J W. Extracellular matrix and perineuronal nets in CNS repair. Dev Neurobiol. (2011) November; 71(11):1073-89.

Pearson and Lipman. Improved Tools for Biological Sequence Analysis, PNAS 85:2444-2448, (1988).

The invention claimed is:

1. A protamine peptide consisting of an amino acid sequence with at least 80% identity to SEQ ID NO: 3.

2. The protamine peptide of claim 1, wherein the amino acid sequence has at least 90% identity to SEQ ID NO: 3.

3. The protamine peptide of claim 1, wherein the amino acid sequence is set forth in SEQ ID NO: 3.

4. A method of promoting neurite outgrowth and/or neuronal regeneration, comprising administering an effective amount of the protamine peptide of claim 1 to a patient in need thereof.

5. The method of claim 4, wherein the subject has experienced a neuronal injury selected from the group consisting of neurodegenerative diseases, traumatic brain injury, spinal cord injury, multiple sclerosis (MS), amyotropic lateral sclerosis (ALS), Parkinson's disease, stroke, peripheral nerve injury, eye injury and skin burn.

6. The method of claim 4, wherein the administration is one or more selected from the group consisting of intracranial, intracerebrospinal, intravenous and topical.

7. The method of claim 4, wherein the administration is one or more selected from the group consisting of direct injection and protamine-bound carrier material implantation.

8. A method of promoting neurite outgrowth and/or neuronal regeneration, comprising administering an effective amount of the protamine peptide of claim 1 to a neural cell in vitro.

9. A protamine peptide, consisting of the amino acid sequence set forth in SEQ ID NO: 10.

10. A method of promoting neurite outgrowth and/or neuronal regeneration, comprising administering an effective amount of the protamine peptide of claim 9 to a patient in need thereof.

11. The method of claim 10, wherein the subject has experienced a neuronal injury selected from the group consisting of neurodegenerative diseases, traumatic brain injury, spinal cord injury, multiple sclerosis (MS), amyotropic lateral sclerosis (ALS), Parkinson's disease, stroke, peripheral nerve injury, eye injury and skin burn.

12. The method of claim 10, wherein the administration is one or more selected from the group consisting of intracranial, intracerebrospinal, intravenous and topical.

13. The method of claim 10, wherein the administration is one or more selected from the group consisting of direct injection and protamine-bound carrier material implantation.

14. A method of promoting neurite outgrowth and/or neuronal regeneration, comprising administering an effective amount of the protamine peptide of claim 9 to a neural cell in vitro.

* * * * *

SEQUENCE LISTING

<160> NUMBER OF SEQ ID NOS: 17

<210> SEQ ID NO 1
<211> LENGTH: 33
<212> TYPE: PRT
<213> ORGANISM: Unknown
<220> FEATURE:
<223> OTHER INFORMATION: Genus/Species name of salmon disclosed by SEQ
      ID NO 1 is not known

<400> SEQUENCE: 1

Met Pro Arg Arg Arg Arg Ser Ser Ser Arg Pro Val Arg Arg Arg Arg
1               5                   10                  15

Arg Pro Arg Val Ser Arg Arg Arg Arg Arg Gly Gly Arg Arg Arg
            20                  25                  30

Arg

<210> SEQ ID NO 2
<211> LENGTH: 6
<212> TYPE: PRT
<213> ORGANISM: Artificial Sequence
<220> FEATURE:
<223> OTHER INFORMATION: synthetic peptide

<400> SEQUENCE: 2

Ala Arg Arg Arg Arg Ser
1               5

<210> SEQ ID NO 3
<211> LENGTH: 25
<212> TYPE: PRT
<213> ORGANISM: Artificial Sequence
<220> FEATURE:
<223> OTHER INFORMATION: peptide

<400> SEQUENCE: 3

Ser Arg Pro Val Arg Arg Arg Arg Pro Arg Val Ser Arg Arg
1               5                   10                  15

Arg Arg Arg Gly Gly Arg Arg Arg
            20                  25

<210> SEQ ID NO 4
<211> LENGTH: 13
<212> TYPE: PRT
<213> ORGANISM: Artificial Sequence
<220> FEATURE:
<223> OTHER INFORMATION: peptide

<400> SEQUENCE: 4

Ser Arg Pro Val Arg Arg Arg Arg Pro Arg Val Ser
1               5                   10

<210> SEQ ID NO 5
<211> LENGTH: 8
<212> TYPE: PRT
<213> ORGANISM: Artificial Sequence
<220> FEATURE:
<223> OTHER INFORMATION: peptide

<400> SEQUENCE: 5

Ser Arg Arg Arg Arg Arg Arg Gly
1               5

<210> SEQ ID NO 6
<211> LENGTH: 6

-continued

```
<212> TYPE: PRT
<213> ORGANISM: Artificial Sequence
<220> FEATURE:
<223> OTHER INFORMATION: peptide

<400> SEQUENCE: 6

Arg Arg Arg Arg Arg Arg
1               5

<210> SEQ ID NO 7
<211> LENGTH: 4
<212> TYPE: PRT
<213> ORGANISM: Artificial Sequence
<220> FEATURE:
<223> OTHER INFORMATION: peptide

<400> SEQUENCE: 7

Arg Arg Arg Arg
1

<210> SEQ ID NO 8
<211> LENGTH: 6
<212> TYPE: PRT
<213> ORGANISM: Artificial Sequence
<220> FEATURE:
<223> OTHER INFORMATION: peptide

<400> SEQUENCE: 8

Ala Lys Lys Lys Lys Ser
1               5

<210> SEQ ID NO 9
<211> LENGTH: 6
<212> TYPE: PRT
<213> ORGANISM: Artificial Sequence
<220> FEATURE:
<223> OTHER INFORMATION: peptide

<400> SEQUENCE: 9

Lys Lys Lys Lys Lys Lys
1               5

<210> SEQ ID NO 10
<211> LENGTH: 14
<212> TYPE: PRT
<213> ORGANISM: Artificial Sequence
<220> FEATURE:
<223> OTHER INFORMATION: peptide

<400> SEQUENCE: 10

Val Ser Arg Arg Arg Arg Arg Gly Gly Arg Arg Arg Arg
1               5                   10

<210> SEQ ID NO 11
<211> LENGTH: 51
<212> TYPE: PRT
<213> ORGANISM: Homo sapiens

<400> SEQUENCE: 11

Met Ala Arg Tyr Arg Cys Cys Arg Ser Gln Ser Arg Ser Arg Tyr Tyr
1               5                   10                  15

Arg Gln Arg Gln Arg Ser Arg Arg Arg Arg Arg Ser Cys Gln Thr
            20                  25                  30

Arg Arg Arg Ala Met Arg Cys Cys Arg Pro Arg Tyr Arg Pro Arg Cys
        35                  40                  45
```

Arg Arg His
    50

<210> SEQ ID NO 12
<211> LENGTH: 33
<212> TYPE: PRT
<213> ORGANISM: Oncorhynchus keta

<400> SEQUENCE: 12

Met Pro Arg Arg Arg Ser Ser Ser Arg Pro Val Arg Arg Arg
1               5                   10                  15

Arg Pro Arg Val Ser Arg Arg Arg Arg Arg Gly Gly Arg Arg Arg
                20                  25                  30

Arg

<210> SEQ ID NO 13
<211> LENGTH: 51
<212> TYPE: PRT
<213> ORGANISM: Mus musculus

<400> SEQUENCE: 13

Met Ala Arg Tyr Arg Cys Cys Arg Ser Lys Ser Arg Ser Arg Cys Arg
1               5                   10                  15

Arg Arg Arg Arg Arg Cys Arg Arg Arg Arg Arg Cys Cys Arg Arg
                20                  25                  30

Arg Arg Arg Arg Cys Cys Arg Arg Arg Ser Tyr Thr Ile Arg Cys
            35                  40                  45

Lys Lys Tyr
    50

<210> SEQ ID NO 14
<211> LENGTH: 51
<212> TYPE: PRT
<213> ORGANISM: Rattus norvegicus

<400> SEQUENCE: 14

Met Ala Arg Tyr Arg Cys Cys Arg Ser Lys Ser Arg Ser Arg Cys Arg
1               5                   10                  15

Arg Arg Arg Arg Arg Cys Arg Arg Arg Arg Arg Cys Cys Arg Arg
                20                  25                  30

Arg Arg Arg Arg Cys Cys Arg Arg Arg Ser Tyr Thr Phe Arg Cys
            35                  40                  45

Lys Arg Tyr
    50

<210> SEQ ID NO 15
<211> LENGTH: 50
<212> TYPE: PRT
<213> ORGANISM: Equus caballus

<400> SEQUENCE: 15

Met Ala Arg Tyr Arg Cys Cys Arg Ser Gln Ser Gln Ser Arg Cys Arg
1               5                   10                  15

Arg Arg Arg Arg Arg Cys Arg Arg Arg Arg Arg Ser Val Arg
                20                  25                  30

Gln Arg Arg Val Cys Cys Arg Arg Tyr Thr Val Leu Arg Cys Arg Arg
            35                  40                  45

Arg Arg
    50

```
<210> SEQ ID NO 16
<211> LENGTH: 47
<212> TYPE: PRT
<213> ORGANISM: Orcinus orca

<400> SEQUENCE: 16

Met Ala Arg Asn Arg Cys Arg Ser Pro Ser Gln Ser Arg Cys Arg Arg
1               5                   10                  15

Pro Arg Arg Arg Cys Arg Arg Arg Ile Arg Cys Cys Arg Arg Gln Arg
            20                  25                  30

Arg Val Cys Cys Arg Arg Tyr Thr Thr Thr Arg Cys Ala Arg Gln
        35                  40                  45

<210> SEQ ID NO 17
<211> LENGTH: 51
<212> TYPE: PRT
<213> ORGANISM: Ovis aries

<400> SEQUENCE: 17

Met Ala Arg Tyr Arg Cys Cys Leu Thr His Ser Arg Ser Arg Cys Arg
1               5                   10                  15

Arg Arg Arg Arg Arg Arg Cys Arg Arg Arg Arg Arg Phe Gly Arg
            20                  25                  30

Arg Arg Arg Arg Arg Val Cys Cys Arg Arg Tyr Thr Val Val Arg Cys
        35                  40                  45

Thr Arg Gln
    50
```